United States Patent
Biel et al.

(10) Patent No.: US 10,716,331 B2
(45) Date of Patent: Jul. 21, 2020

(54) ELECTRONIC SMOKING DEVICE WITH A GLASS CAPILLARY TUBE

(71) Applicant: Fontem Holdings 1 B.V., Amsterdam (NL)

(72) Inventors: Stefan Biel, Hamburg (DE); Vaclav Borkovec, Hamburg (DE); Lutz Deichmann, Hamburg (DE); Neha Daryani, Hamburg (DE)

( * ) Notice: Subject to any disclaimer, the term of this patent is extended or adjusted under 35 U.S.C. 154(b) by 239 days.

(21) Appl. No.: 15/750,116

(22) PCT Filed: Aug. 5, 2016

(86) PCT No.: PCT/EP2016/068770
§ 371 (c)(1),
(2) Date: Feb. 2, 2018

(87) PCT Pub. No.: WO2017/021536
PCT Pub. Date: Feb. 9, 2017

(65) Prior Publication Data
US 2018/0220707 A1 Aug. 9, 2018

(30) Foreign Application Priority Data

Aug. 6, 2015 (EP) .................................. 15180009

(51) Int. Cl.
*A24F 13/00* (2006.01)
*A24F 47/00* (2020.01)
(Continued)

(52) U.S. Cl.
CPC ......... *A24F 47/008* (2013.01); *A61M 11/042* (2014.02); *A61M 15/06* (2013.01);
(Continued)

(58) Field of Classification Search
CPC ...................................................... H01R 47/00
(Continued)

(56) References Cited

U.S. PATENT DOCUMENTS

| 4,765,347 A | 8/1988 | Sensabaugh, Jr. et al. |
| 2011/0303231 A1* | 12/2011 | Li ........................ A24F 47/008 131/329 |

(Continued)

FOREIGN PATENT DOCUMENTS

| CN | 102264249 A | 11/2011 |
| CN | 104126878 A | 11/2014 |

(Continued)

*Primary Examiner* — Phuong K Dinh
(74) *Attorney, Agent, or Firm* — Dykema Gossett PLLC

(57) ABSTRACT

An electronic smoking device (10) includes a battery portion (12) including an electric power source (18), an atomizer/liquid reservoir portion (14) having a mouthpiece opening (36) in an end, a liquid reservoir (34) for accommodating a liquid, and a glass capillary tube (46). The glass capillary tube (46) comprises a first open end (48) arranged inside the liquid reservoir (34) and an outlet portion (50), wherein the glass capillary tube (46) is adapted to transport liquid from the first open end (48) to the outlet portion (50) by capillary force. The electronic smoking device (10) further includes an atomizer (26) arranged at the outlet portion (50) such that is operable to vaporize liquid at the outlet portion (50) to create an aerosol.

14 Claims, 7 Drawing Sheets

(51) Int. Cl.
*A61M 11/04* (2006.01)
*A61M 15/06* (2006.01)

(52) U.S. Cl.
CPC ............... *A61M 2205/3653* (2013.01); *A61M 2205/8206* (2013.01)

(58) Field of Classification Search
USPC ................................................. 131/329, 328
See application file for complete search history.

(56) References Cited

U.S. PATENT DOCUMENTS

| | | |
|---|---|---|
| 2011/0309157 A1 | 12/2011 | Yang et al. |
| 2013/0081642 A1 | 4/2013 | Safari |
| 2013/0213418 A1 | 8/2013 | Tucker et al. |
| 2015/0144145 A1 | 5/2015 | Chang et al. |
| 2016/0021931 A1* | 1/2016 | Hawes ................. A61M 11/042 131/328 |

FOREIGN PATENT DOCUMENTS

| | | |
|---|---|---|
| CN | 104254356 A | 12/2014 |
| CN | 104302197 A | 1/2015 |
| CN | 104720114 A | 6/2015 |
| WO | 2014153515 A1 | 9/2014 |

* cited by examiner

ELECTRONIC SMOKING DEVICE WITH A GLASS CAPILLARY TUBE

FIELD OF INVENTION

The present invention relates generally to electronic smoking devices and in particular electronic cigarettes.

BACKGROUND OF THE INVENTION

An electronic smoking device, such as an electronic cigarette (e-cigarette), usually has a housing accommodating an electric power source (e.g. a single use battery or a rechargeable battery), and an electrically operable atomizer. The atomizer vaporizes or atomizes liquid supplied from a reservoir and provides vaporized or atomized liquid as an aerosol. Control electronics control the activation of the atomizer. In many electronic cigarettes, an airflow sensor is provided within the electronic smoking device which detects a user puffing on the device (e.g., by sensing an under-pressure or an air flow pattern through the device). The airflow sensor indicates or signals the puff to the control electronics. Alternatively, a button may be used to switch on the electronic smoking device to generate a puff of flavor. When a puff is detected, the control electronics supplies electrical power to the atomizer thereby creating vaporized liquid as an aerosol.

To date, fibrous materials like sponges or string wicks suffer from inconsistent liquid delivery as the storage reservoir becomes depleted.

SUMMARY OF THE INVENTION

In accordance with one aspect of the present invention there is provided an electronic smoking device including a battery portion including an electric power source and an atomizer/liquid reservoir portion having a mouthpiece opening in an end. The electronic smoking device further includes a liquid reservoir for accommodating a liquid and one or more glass capillary tube(s), wherein the glass capillary tube comprises a first open end arranged inside the liquid reservoir and an outlet portion, wherein the glass capillary tube is adapted to transport liquid from the first open end to the outlet portion by capillary force. The electronic smoking device further includes an atomizer arranged at the outlet portion such that is operable to vaporize liquid at the outlet portion to create an aerosol.

The characteristics, features and advantages of this invention and the manner in which they are obtained as described above, will become more apparent and be more clearly understood in connection with the following description of exemplary embodiments, which are explained with reference to the accompanying drawings.

BRIEF DESCRIPTION OF THE DRAWINGS

In the drawings, same element numbers indicate same elements in each of the views.

DESCRIPTION OF THE PREFERRED EMBODIMENTS

Figure 1:
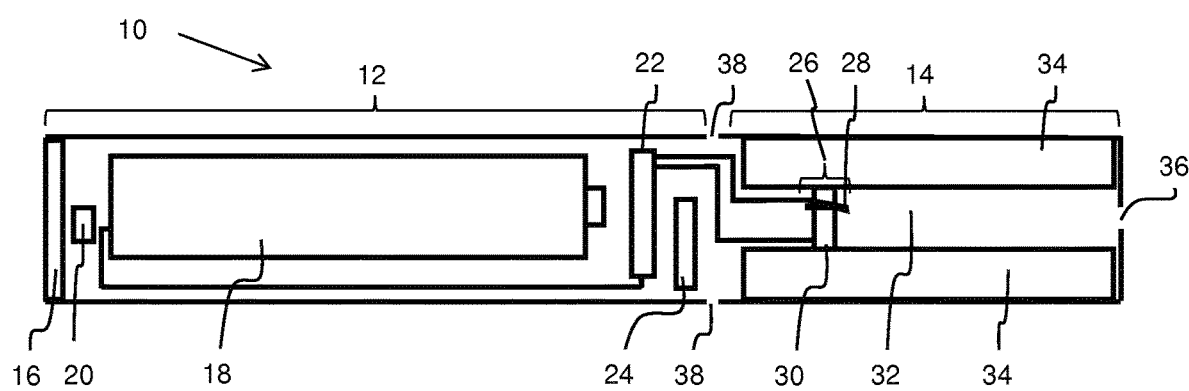
FIG. 1 is a schematic cross-sectional illustration of an exemplary e-cigarette.

Throughout the following, an electronic smoking device will be exemplarily described with reference to an e-cigarette. As is shown in FIG. 1, an e-cigarette 10 typically has a housing comprising a cylindrical hollow tube having an end cap 16. The cylindrical hollow tube may be single piece or a multiple piece tube. In FIG. 1, the cylindrical hollow tube is shown as a two piece structure having a battery portion 12 and an atomizer/liquid reservoir portion 14. Together the battery portion 12 and the atomizer/liquid reservoir portion 14 form a cylindrical tube which is approximately the same size and shape as a conventional cigarette, typically about 100 mm with a 7.5 mm diameter, although lengths may range from 70 to 150 or 180 mm, and diameters from 5 to 40 mm.

The battery portion 12 and atomizer/liquid reservoir portion 14 are typically made of steel or hardwearing plastic and act together with the end cap 16 to provide a housing to contain the components of the e-cigarette 10. The battery portion 12 and an atomizer/liquid reservoir portion 14 may be configured to fit together by a friction push fit, a snap fit, or a bayonet attachment, magnetic fit, or screw threads. The end cap 16 is provided at the front end of the battery portion 12. The end cap 16 may be made from translucent plastic or other translucent material to allow an LED 20 positioned near the end cap to emit light through the end cap. The end cap can be made of metal or other materials that do not allow light to pass. The battery portion and atomizer portions may also be fused together as a single product that can not be disconnected by the consumer, and this may be sold as a disposable device.

An air inlet may be provided in the end cap, at the edge of the inlet next to the cylindrical hollow tube, anywhere along the length of the cylindrical hollow tube, or at the connection of the battery portion 12 and the atomizer/liquid reservoir portion 14. FIG. 1 shows a pair of air inlets 38 provided at the intersection between the battery portion 12 and the atomizer/liquid reservoir portion 14.

A battery 18, a light emitting diode (LED) 20, control electronics 22 and optionally an airflow sensor 24 are provided within the cylindrical hollow tube battery portion 12. The battery 18 is electrically connected to the control electronics 22, which are electrically connected to the LED 20 and the airflow sensor 24. In this example the LED 20 is at the front end of the battery portion 12, adjacent to the end cap 16 and the control electronics 22 and airflow sensor 24 are provided in the central cavity at the other end of the battery 18 adjacent the atomizer/liquid reservoir portion 14.

The airflow sensor 24 acts as a puff detector, detecting a user puffing or sucking on the atomizer/liquid reservoir portion 14 of the e-cigarette 10. The airflow sensor 24 can be any suitable sensor for detecting changes in airflow or air pressure such a microphone switch including a deformable membrane which is caused to move by variations in air pressure. Alternatively the sensor may be a Hall element or an electro-mechanical sensor.

The control electronics 22 are also connected to an atomizer 26. In the example shown, the atomizer 26 includes a heating coil 28 which is wrapped around a wick 30 extending across a central passage 32 of the atomizer/liquid reservoir portion 14. The coil 28 may be positioned anywhere in the atomizer 26 and may be transverse or parallel to the liquid reservoir 34. The wick 30 and heating coil 28 do not completely block the central passage 32. Rather an air gap is provided on either side of the heating coil 28 enabling air to flow past the heating coil 28 and the wick 30. The atomizer may alternatively use other forms of heating elements, such as ceramic heaters, or fiber or mesh material heaters. Nonresistance heating elements such as sonic, piezo and jet spray may also be used in the atomizer in place of the heating coil.

The central passage 32 is surrounded by a cylindrical liquid reservoir 34 with the ends of the wick 30 abutting or extending into the liquid reservoir 34. The wick 30 may be a porous material such as a bundle of fiberglass fibers, with liquid in the liquid reservoir 34 drawn by capillary action from the ends of the wick 30 towards the central portion of the wick 30 encircled by the heating coil 28.

The liquid reservoir 34 may alternatively include wadding soaked in liquid which encircles the central passage 32 with the ends of the wick 30 abutting the wadding. In other embodiments the liquid reservoir 34 may comprise a toroidal cavity arranged to be filled with liquid and with the ends of the wick 30 extending into the toroidal cavity.

An air inhalation port 36 is provided at the back end of the atomizer/liquid reservoir portion 14 remote from the end cap 16. The inhalation port 36 may be formed from the cylindrical hollow tube atomizer/liquid reservoir portion 14 or may be formed in an end cap.

In use, a user sucks on the e-cigarette 10. This causes air to be drawn into the e-cigarette 10 via one or more air inlets, such as air inlets 38 and to be drawn through the central passage 32 towards the air inhalation port 36. The change in air pressure which arises is detected by the airflow sensor 24 which generates an electrical signal that is passed to the control electronics 22. In response to the signal, the control electronics 22 activate the heating coil 28 which causes liquid present in the wick 30 to be vaporized creating an aerosol (which may comprise gaseous and liquid components) within the central passage 32. As the user continues to suck on the e-cigarette 10, this aerosol is drawn through the central passage 32 and inhaled by the user. At the same time the control electronics 22 also activate the LED 20 causing the LED 20 to light up which is visible via the translucent end cap 16 mimicking the appearance of a glowing ember at the end of a conventional cigarette. As liquid present in the wick 30 is converted into an aerosol more liquid is drawn into the wick 30 from the liquid reservoir 34 by capillary action and thus is available to be converted into an aerosol through subsequent activation of the heating coil 28.

Some e-cigarette are intended to be disposable and the electric power in the battery 18 is intended to be sufficient to vaporize the liquid contained within the liquid reservoir 34 after which the e-cigarette 10 is thrown away. In other embodiments the battery 18 is rechargeable and the liquid reservoir 34 is refillable. In the cases where the liquid reservoir 34 is a toroidal cavity, this may be achieved by refilling the liquid reservoir 34 via a refill port. In other embodiments the atomizer/liquid reservoir portion 14 of the e-cigarette 10 is detachable from the battery portion 12 and a new atomizer/liquid reservoir portion 14 can be fitted with a new liquid reservoir 34 thereby replenishing the supply of liquid. In some cases, replacing the liquid reservoir 34 may involve replacement of the heating coil 28 and the wick 30 along with the replacement of the liquid reservoir 34. A replaceable unit comprising the atomizer 26 and the liquid reservoir 34 is called a cartomizer.

The new liquid reservoir 34 may be in the form of a cartridge having a central passage 32 through which a user inhales aerosol. In other embodiments, aerosol may flow around the exterior of the cartridge 32 to an air inhalation port 36.

Of course, in addition to the above description of the structure and function of a typical e-cigarette 10, variations also exist. For example, the LED 20 may be omitted. The airflow sensor 24 may be placed adjacent the end cap 16 rather than in the middle of the e-cigarette. The airflow sensor 24 may be replaced with a switch which enables a user to activate the e-cigarette manually rather than in response to the detection of a change in air flow or air pressure.

Different types of atomizers may be used. Thus for example, the atomizer may have a heating coil in a cavity in the interior of a porous body soaked in liquid. In this design aerosol is generated by evaporating the liquid within the porous body either by activation of the coil heating the porous body or alternatively by the heated air passing over or through the porous body. Alternatively the atomizer may use a piezoelectric atomizer to create an aerosol either in combination or in the absence of a heater.

Figure 2:
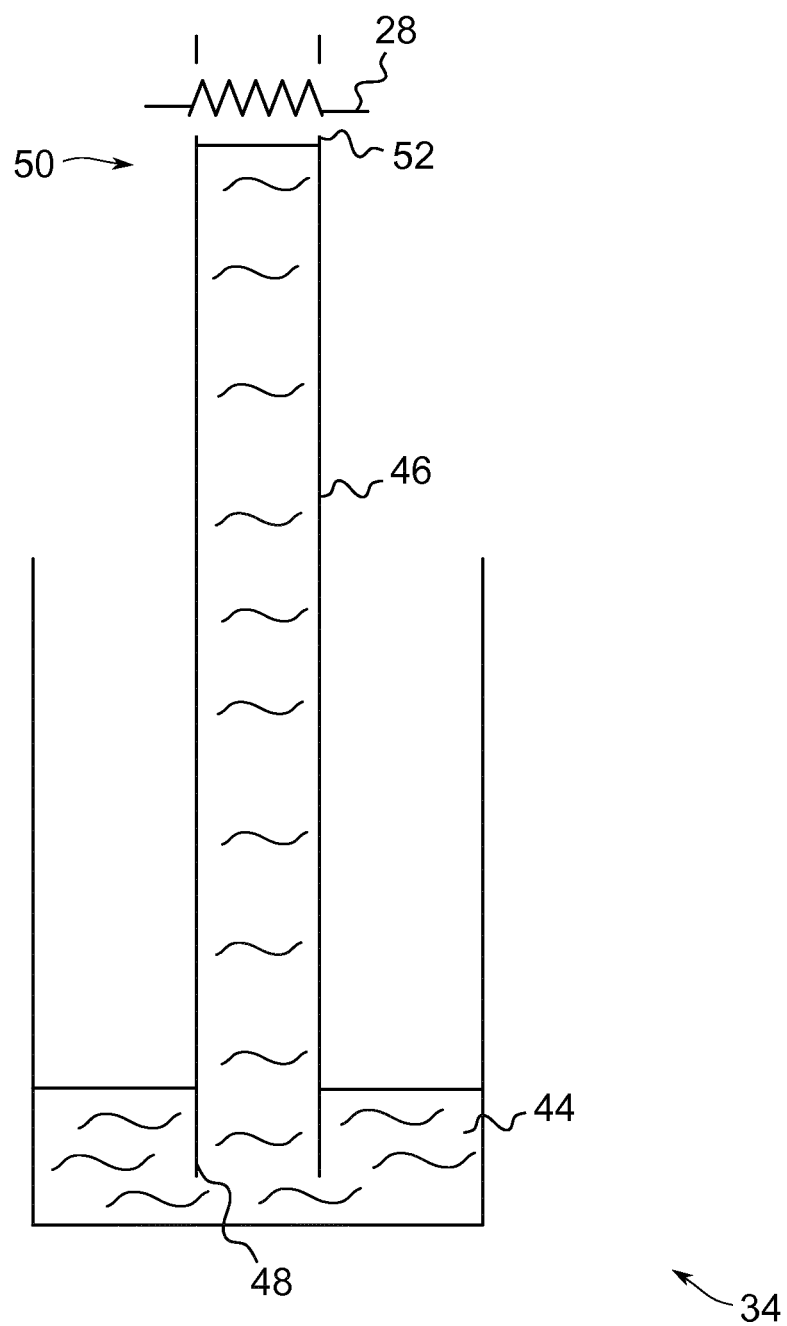
FIG. 2 is a schematic illustration of a further exemplary embodiment of a liquid reservoir.

FIG. 2 shows an exemplary embodiment of the liquid reservoir 34. The liquid reservoir 34 is adapted to accommodate liquid 44.

Such liquids are usually a mixture of propylene glycol, glycerine and nicotine. Some liquids may have similar ingredients but without nicotine. In addition, flavoured materials may be added to the liquid 44, for example esters, such as isoamyl acetate, linalyl acetate, isoamyl propionate, linalyl butyrate and the like or natural essential oils as plant essential oils, such as spearmint, peppermint, cassia, jasmine and the like or animal essential oils, such as musk, amber, civet, castor and the like or simple flavouring materials, such as anethole, limonene, linalool, eugenol and the like or hydrophilic flavour components such as a leaf tobacco extract or natural plant flavouring materials such as licorice, St. John's wort, a plum extract, a peach extract and the like or acids such as a malic acid, tartaric acid, citric acid and the like or sugars such as glucose, fructose, isomerized sugar and the like or polyhydric alcohols such as propylene glycol, glycerol, sorbitol and the like. It is also possible to combine different flavoured materials as mentioned above into new flavoured materials.

Liquid 44 from the liquid reservoir 34 is delivered or provided to the heating element or heating wire 28 of the atomizer 26. Here, a glass capillary tube 46 is provided for delivery of the liquid 44 instead of a wick which is usually provided. Thus, capillary force is used for delivery of liquid 44 to the heating wire 28. The glass capillary tube 46 may preferably be inflexible or stiff. The thickness of the glass wall of the glass capillary tube 46 may be such that no bending of the glass capillary tube 46 is possible. Such embodiment may have the advantage that mechanical stability is enhanced and steady, reliable liquid transportation is provided.

The height that a liquid travels inside a capillary tube 46 is only dependent on the initial height of liquid in the reservoir 34, the geometry of the tube and the properties of the liquid.

The height h of a liquid column in a capillary tube 46 is given by the following formula $$h = \frac{2\gamma\cos\theta}{\rho g r},$$

where $\gamma$ is the liquid-air surface tension, $\theta$ is the contact angle, $\rho$ is the density of the liquid, g is the local acceleration due to gravity (length/square of time), and r is the radius of the capillary tube. It is known that for a smaller radius of the capillary tube 46 the liquid 44 raises higher or travels further inside the capillary tube 46.

The term 'h' in the equation above refers to the difference in height between the water in the capillary (h1) and the water in the reservoir (h2), h=h1−h2. The distance that the liquid travels in the tube is not dependant on the starting height of the reservoir because it is a constant distance, however the position that the liquid rises h1 inside the tube will change with respect to the length of the tube.

Such a wickless design, implementing a capillary tube 46 with a very small radius 'r', may have the advantage of constant liquid dosages irrespective of the amount of remaining liquid in the reservoir. The orientation of the capillary system, i.e. the glass capillary tube and the liquid reservoir or liquid reservoir, does not affect the delivery performance since capillary forces depends less and less on gravity the smaller the radius 'r' is (see equation).

The capillary tube 46 consists of glass. A first open end 48 of the capillary tube 46 is arranged inside the liquid reservoir 34. The first open end 48 is arranged close to a bottom surface of the liquid reservoir 34 so as to enable best usage of the liquid 44.

A single glass capillary tube 46 is provided. The single glass tube may allow defined dosage or delivery of the liquid as compared to a bundle of glass fibers.

According to FIG. 2 the capillary tube 46 extends in a straight direction from the first open end 48 to an outlet portion 50 which is in this embodiment identical with a second open end 52 of the capillary tube 46. The heating wire 28 of the atomizer 26 is arranged in front of the outlet portion 50 or the second open end 52. The heating wire 28 emits heat when a current is flowing through the wire. The heat vaporizes liquid 44 at a distal end or second open end 52 of the capillary tube 46 thereby creating an aerosol or liquid droplets. The aerosol is drawn towards the air inhalation port.

The capillary tube 46 may have a length of several centimeters, preferably 0.5 to 5 cm. The capillary tube 46 may have a diameter in the range of a few millimeters to several tenths of millimeters, preferably 0.5 to 5 mm. If multiple capillary tubes are used in parallel, the diameter could be much smaller, e.g. tenths of a millimeter. The heating wire 28 may be spaced apart from the second open end 52 or may be located directly at the second open end 52. Further, the heating wire 28 may be located at least partially in the second open end 52.

Figure 3:
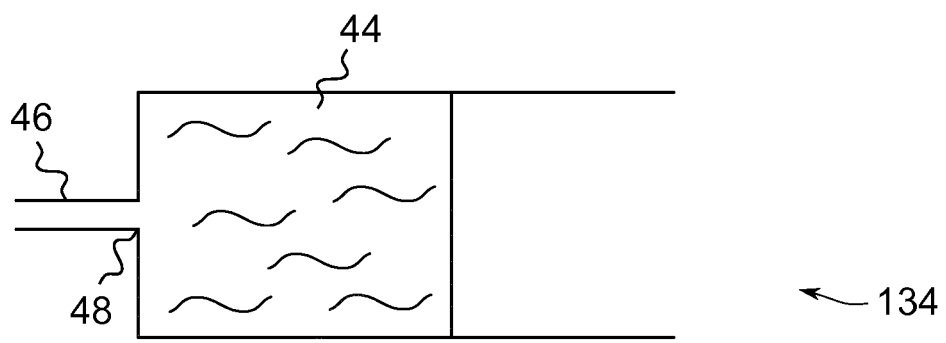
FIG. 3 is a schematic illustration of a further exemplary embodiment of a liquid reservoir.

FIG. 3 shows a further embodiment of the liquid reservoir 134. The liquid reservoir 134 is at least partially filled with a liquid 44. A capillary tube 46 is arranged in connection with the liquid reservoir 134. The capillary tube 46 is arranged at a first side of the liquid reservoir 134. The capillary tube 46 delivers liquid 44 from the liquid reservoir 134 to the heating coil or heating wire of an atomizer which is not depicted in FIG. 3. The liquid reservoir 134 is open at a second end which is opposite to the first end at which the capillary tube 46 is arranged. The open end allows air entering the liquid reservoir 134 so that no vacuum or negative pressure builds up when the liquid 44 is drawn out of the liquid reservoir 134. The liquid 44 is held by its viscosity inside the liquid reservoir. This embodiment may have the advantage that delivery of the liquid 44 is improved. The reservoir may have an adjustable bottom that moves towards the capillary tube as the liquid is depleted to create a self-shrinking reservoir.

The capillary tube 46 reaches to the first end of the liquid reservoir 134. In other words, the first open end 48 of the capillary tube 46 coincides with an opening in the first end of the liquid reservoir 134. This implies that the liquid 44 is delivered from the first end of the liquid reservoir 134. During use of the electronic cigarette, as the liquid reservoir 134 is depleted continuously, a boundary between the liquid 44 and air inside the liquid reservoir 134 moves from the second end of the liquid reservoir 134 to the first end or towards the capillary tube 46.

The liquid reservoir 134 may be designated as a replaceable capsule for the electronic cigarette. The liquid reservoir 134 may have a cylindrical shape wherein the first and second sides may be round end faces. The liquid reservoir 134 may have a rectangular shape. The liquid reservoir 134 may also have an irregular shape adapted to the available space inside the electronic cigarette. The capillary tube 46 may be arranged in the center of the first side.

Figure 4:
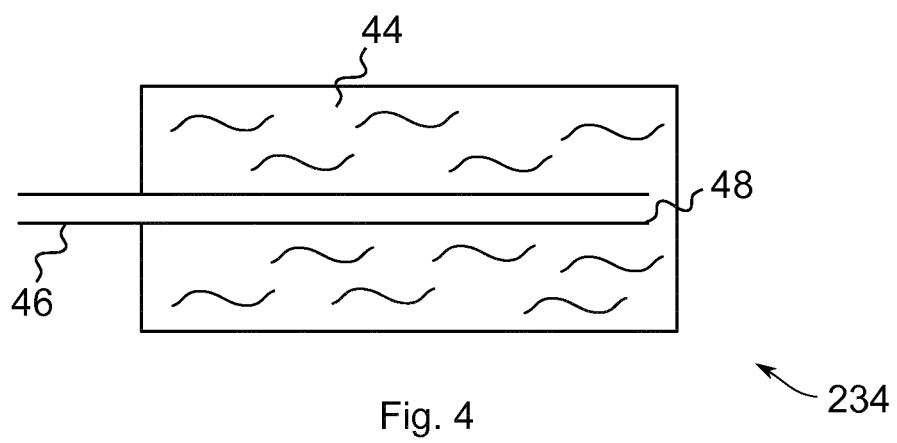
FIG. 4 is a schematic illustration of a further exemplary embodiment of a liquid reservoir.

FIG. 4 shows a further embodiment of a liquid reservoir 234. The liquid reservoir 234 is holding a liquid 44. The liquid reservoir 234 further includes a capillary tube 46 which penetrates a hull or housing of the liquid reservoir 234 so that communication between the liquid reservoir 234 and the outside is achieved. A first open end 48 of the capillary tube 46 reaches close to a second or bottom surface of the liquid reservoir 234. Besides the capillary tube 46 the liquid reservoir 234 is closed such that a housing of the liquid reservoir 234 completely encloses the liquid 44. During use of the electronic cigarette the liquid 44 advances towards the second end of the liquid reservoir 234 at which the first open end 48 of the capillary tube 46 is located. The closed liquid reservoir 234 may have the advantage that the liquid 44 is protected from external influences like inflowing air.

The first open end 48 of the capillary tube 46 may be located at a distance of a few millimeters, preferably 1 to 5 millimeters, to a surface or wall of the liquid reservoir 234. This distance may also have a length of 1 to 5 times, preferably 2 to 3 times of the diameter of the capillary tube 46.

Figure 5:
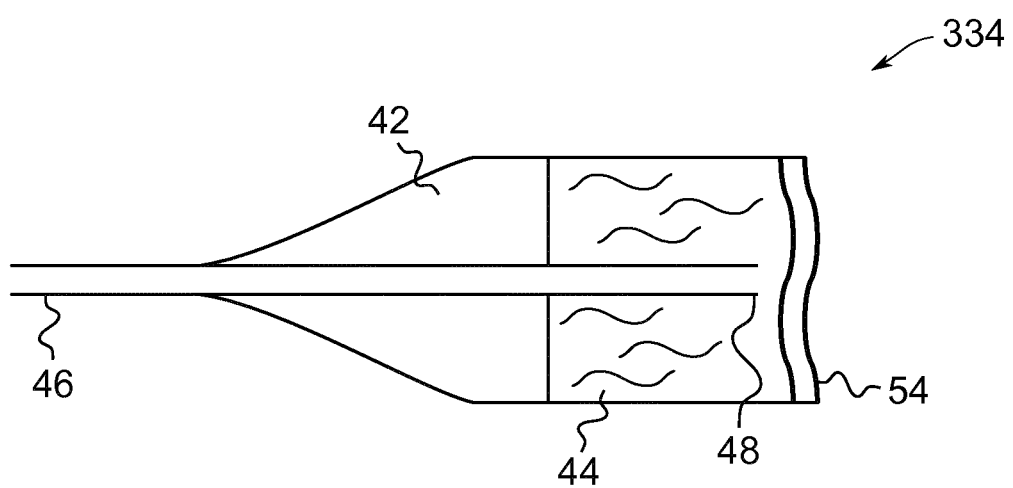
FIG. 5 is a schematic illustration of a further exemplary embodiment of a liquid reservoir.

FIG. 5 shows a further embodiment of a liquid reservoir 334. Again, the liquid reservoir 334 is adapted for containing a liquid 44. A capillary tube 46 reaches with its first open end 48 inside the liquid reservoir 334 for transporting liquid 44 from the first open end 48 to an outlet portion or a second open end of the capillary tube 46 by capillary force. In this embodiment, at least a part of casing of the liquid reservoir 334 includes a semi-permeable membrane 54 allowing air to enter into the liquid reservoir 334 while preventing the liquid 44 to escape from the liquid reservoir 334. The semi-permeable membrane 54 is arranged at a surface or bottom surface of the liquid reservoir 334. Such air-porous sealing may have the advantage of allowing air pressure to equalize inside the liquid reservoir while preventing a liquid leakage.

Further in this embodiment, the liquid reservoir 334 has a shape of a bottle wherein the capillary tube 46 extends through a top end of the liquid reservoir 334 and the semi-porous membrane 54 is located at the bottom portion or bottom end of the liquid reservoir 334. Such shape of the liquid reservoir 334 may have the advantage of easier handling or better integration into an electronic cigarette.

The semi-permeable membrane may cover the complete surface or only parts of the surface of the liquid reservoir. The semi-permeable membrane may also be arranged at other surfaces for example side wall surfaces of the liquid reservoir. The use of one or more semi-permeable membranes 54 is not limited to the bottle shape form of the liquid reservoir 334 as shown in FIG. 5. At least one semi-permeable membrane 54 may be included into liquid reservoirs having for example a cylindrical or rectangular shape.

Figure 6:
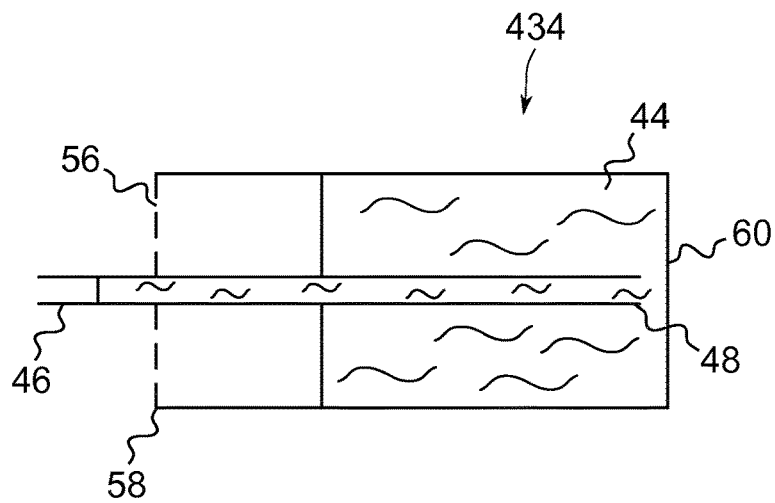
FIG. 6 is a schematic illustration of a further exemplary embodiment of a liquid reservoir.

FIG. 6 shows a further embodiment of a liquid reservoir 434. The liquid reservoir 434 shown in FIG. 6 is similar to the liquid reservoirs 34 of FIG. 2 and 234 of FIG. 4. Accordingly, the liquid reservoir 434 of FIG. 6 is holding liquid 44 and further includes a capillary tube 46 for transporting liquid 44 out of the liquid reservoir 34 by capillary force. In this embodiment, the liquid reservoir 434 includes at least one air inlet 56. Such arrangement may have the advantage that air can enter the liquid reservoir 34 through the at least one air inlet 56 so that the air pressure inside the liquid reservoir 434 is equalized. This may improve capillary drawing of the liquid 44 as no vacuum is built up inside the liquid reservoir 434. Here, four air inlets 56 are arranged at a first side 58 of the liquid reservoir 434 through which the capillary tube 46 extends. The air inlets 56 are arranged opposed to the first open end 48 of the capillary tube 46. In other words, the first side 58 with the air inlets 56 is further away from the first open end 48 of the capillary tube 46 than a second side 60.

Instead of providing four air inlets 56 any other number of air inlets 56 may be provided. Preferably, a number between one and six air inlets 56 is provided. In case of an even number of air inlets 56 the air inlets 56 may be arranged opposed with regard to the capillary tube 46. The at least one air inlet 56 may have a diameter allowing air to enter into the liquid reservoir 434 and preventing the liquid 44 to escape from the liquid reservoir 434. Such size or diameter of the air inlet 56 prevents leakage of the liquid 44 due to the viscosity of the liquid 44. Such an arrangement may advantageously allow the capillary forces continuing to work as no vacuum may be created by liquid depletion.

Figure 7:
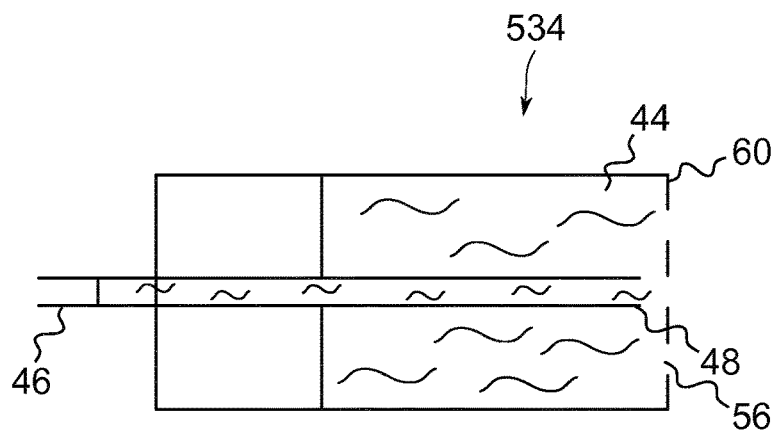
FIG. 7 is a schematic illustration of a further exemplary embodiment of a liquid reservoir.

FIG. 7 shows a further embodiment of the liquid reservoir 534. The liquid reservoir 534 shown in FIG. 7 is basically comparable with the liquid reservoir 434 shown in FIG. 6. In FIG. 7, the air inlets 56 are arranged at the second side 60 of the liquid reservoir 534. Three air inlets 56 are included in the second side or second surface 60. In contrast to FIG. 6, the air inlets 56 are located at the surface 60 close to the first open end 48 of the capillary tube 46. This implies, that the air inlets 56 are covered by liquid 44. During use of the electronic cigarette, i.e. depletion of the liquid 44, air is drawn through the air inlets 56 into the liquid reservoir 534. Inside the liquid reservoir 34 air may migrate through the liquid 44 into the already emptied portion of the liquid reservoir 534 thereby equalizing the air pressure inside the liquid reservoir 534.

While the air inlets 56 have been shown in FIGS. 6 and 7 at first and second sides 58 and 60 at least one or all of the air inlets 56 may be arranged at other sides or surfaces of the liquid reservoir.

Figure 8:
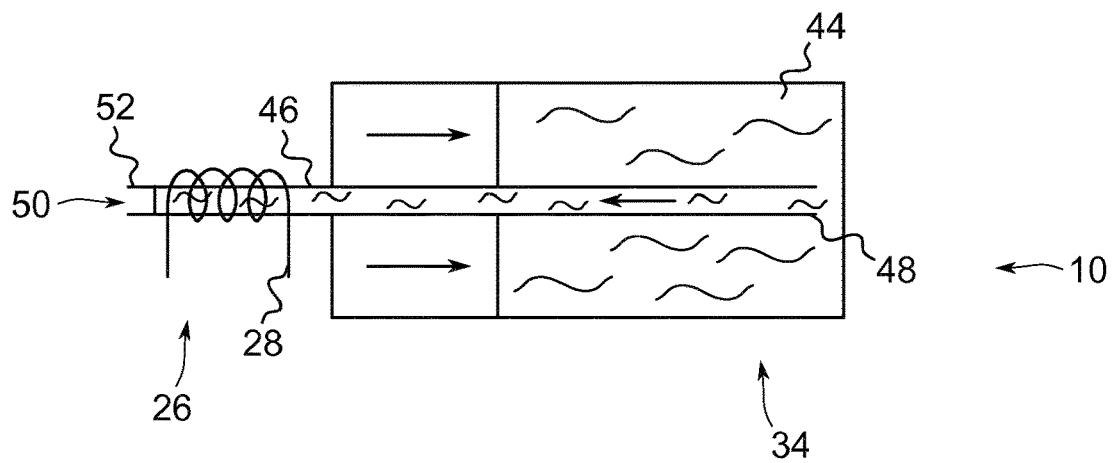
FIG. 8 is a schematic illustration of a further exemplary embodiment of a liquid reservoir.

FIG. 8 shows a part of the electronic cigarette 10, namely the atomizer 26 with its heating coil 28 and a liquid reservoir 34 containing liquid 44. The electronic cigarette 10 further includes a capillary tube 46 adapted for transporting liquid 44 out of the liquid reservoir 34 to the heating coil or heating wire 28 of the atomizer 26. To achieve such functionality a first open end 48 of the capillary tube is arranged inside the liquid reservoir 34 such that the first open end 48 is covered by liquid 44. A second open end 52 which coincides with the outlet portion 50 of the capillary tube 46 in this embodiment is arranged outside the liquid reservoir 34. At the outlet portion 50 a heating wire 28 of the atomizer 26 is wound around a peripheral surface of the glass capillary tube 46. As the liquid 44 is drawn by capillary force close to the outlet portion 50 liquid is present inside the capillary tube 46 in an area where the heating wire is wound around the capillary tube 46.

Figure 9:
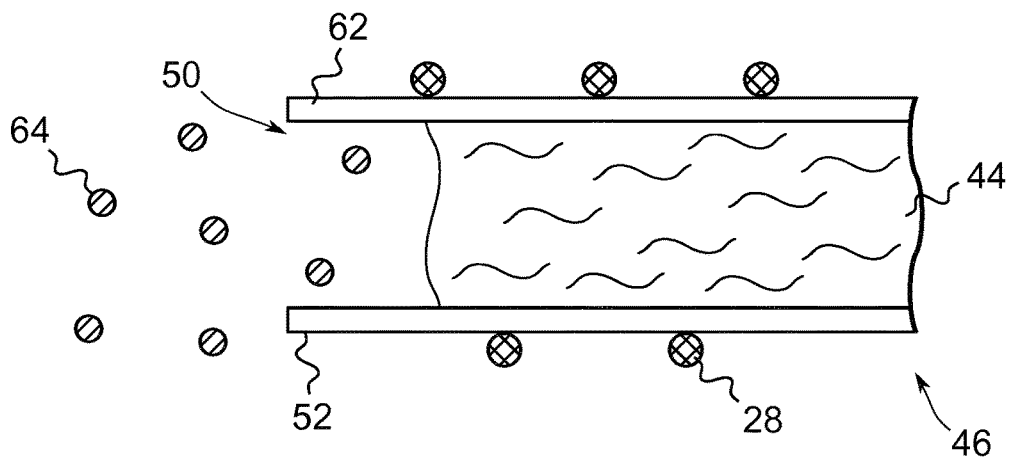
FIG. 9 is a schematic illustration of a part of a glass capillary tube.

FIG. 9 shows the second open end 52 of the capillary tube 46 with the wound heating wire 28 in greater detail. The liquid 44 reaches inside the capillary tube 46 close to the second open end 52. Close to the second open end 52 the heating coil 28 is wound around the glass wall 62 of the capillary tube 46 in a contact portion. The heating coil or heating wire 28 is in direct contact with a glass wall 62 of the capillary tube 46. All or at least parts of the windings 28 enclose liquid 44 inside the glass wall 62.

Upon actuation of the electronic cigarette a current flows through the heating wire 28 thereby heating the heating wire 28. The heat is transmitted through the glass wall 62 into the liquid 44. Thereby the liquid 44 is vaporized. During vaporization liquid droplets 64 or an aerosol is generated and injected out of the outlet portion 50. As the liquid 44 is continuously vaporized in the area of the heating coil 28 further liquid is delivered from the liquid reservoir 34 towards the second open end 52 of the glass capillary tube 46. Such arrangement may have the advantage of easy and inexpensive production as the glass capillary tube consists of a simple glass tube.

Figure 10:
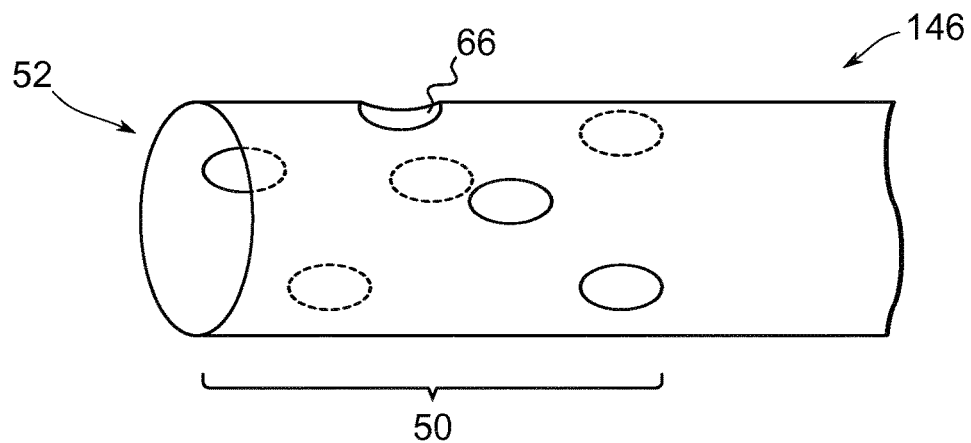
FIG. 10 is a schematic illustration of a part of a further glass capillary tube.

FIG. 10 shows a further embodiment of the capillary tube 146. For easier understanding only a part of the glass capillary tube 146 at its second open end 52 is depicted. The capillary tube 146 includes a glass capillary tube having a second open end 52. Towards the second open end 52 the glass capillary tube 146 includes at least one opening 66 in a peripheral surface or the wall of the glass capillary tube 146. According to this embodiment a plurality of circular openings 66 is arranged circumferentially at the peripheral surface of the capillary tube 146. The outlet portion 50 is defined by the openings 66. In the area of the outlet portion 50 the heating coil 28 (not shown for the sake of clarity) is wound around the glass body of the capillary tube 146.

The size or diameter of the opening 66 is too small for the viscous liquid 44 to leave the glass capillary tube 146. The openings 66, however, are large enough to allow a gas exchange from the inside of the glass capillary tube 146 to the outside and/or vice versa. In embodiments where the holes are large enough to allow liquid to move across the holes, the holes would serve the function of 'limiting' the liquid height inside the capillary tube in order to maintain a constant height for effective heating.

When the heating wire 28 is heated by a current flowing through the heating wire 28 heat is transferred through the glass body of the capillary tube 146 inside the capillary tube 146 thereby vaporizing the liquid 44 present in that part of the capillary tube 146. The liquid 44 is vaporized by the heat so that fluid droplets are generated when the vaporized liquid condenses. The fluid droplets or the vaporized gas escapes the glass capillary tube 146 through the openings 66. Such arrangement may have the advantage of easier and more even gas or droplet escape. This may prevent uneven aerosol delivery or spitting.

The outlet portion 50 may also include the second open end 52 so that the aerosol is emitted through the openings 66 and the second open end 52. Alternatively, the second end may be closed so that the aerosol is leaving the capillary tube 146 solely through the openings 66.

Figure 11:
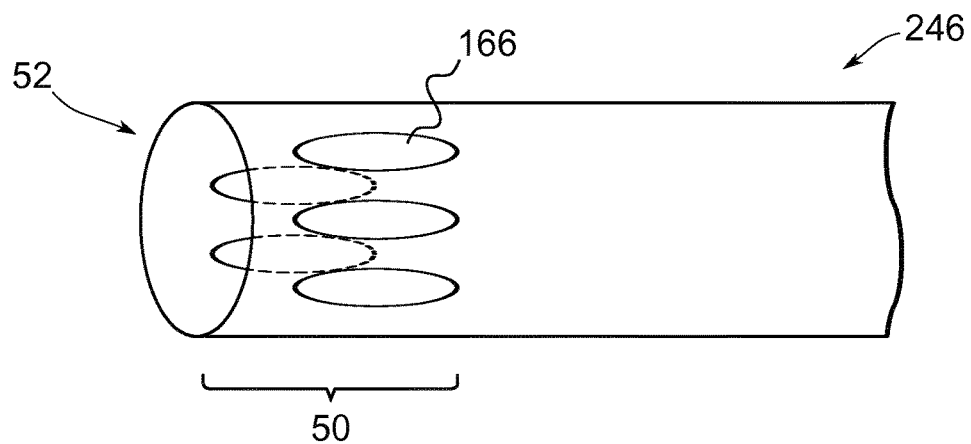
FIG. 11 is a schematic illustration of a part of a further glass capillary tube.

FIG. 11 shows a further embodiment of the capillary tube 246. The glass capillary tube 246 of FIG. 11 is basically similar to the capillary tube 146 shown in FIG. 10. The glass capillary tube 246 also includes openings 166 located close to the second open end 52. According to this embodiment the openings 166 have an elliptical shape or the form of a slit. The long axis of the ellipse is parallel to a longitudinal axis of the glass capillary tube 246. The openings 166 are evenly distributed circumferentially at the outer peripheral surface of the glass capillary tube 246. The openings 166 are arranged at the same distance to the second open end 52 of the glass capillary tube 246. The outlet portion for the aerosol or the fluid droplets is defined by the openings 166 or by the opening 166 in conjunction with the second open end 52.

The openings 166 may have different shapes for example as to improve the flow of gas. Further, the lengths in an axial direction of the openings 166 may be adapted to the length of the heating wire 28 such that the outlet portion 50 coincides with a heating wire contact area.

Figure 12:
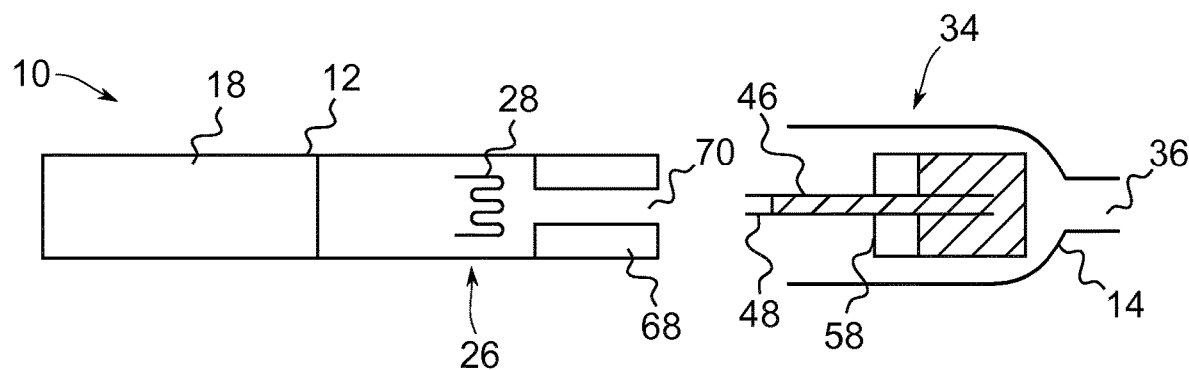
FIG. 12 is a schematic cross-sectional illustration of a further exemplary e-cigarette.

FIG. 12 depicts an exemplary embodiment of an e-cigarette 10 depicted in a disassembled state. A battery portion 12 of the e-cigarette 10 includes a battery and an atomizer 26 with a heating coil or heating wire 28. The e-cigarette 10 further includes a mouth piece portion 14 which is shown disassembled from the battery portion 12. Prior to using the e-cigarette 10 the mouth piece portion 14 is attached to the battery portion 12. The mouth piece portion 14 includes a liquid reservoir 34 or any other liquid reservoir shown in the previous Figures. The liquid reservoir 34 includes a glass capillary tube 46 for drawing liquid out of the liquid reservoir 34 and delivering it to a first open end 48 of the liquid reservoir 34.

In an assembled state of the e-cigarette 10, i.e. when the mouth piece portion 14 and the battery portion 12 are connected with each other, the glass capillary tube 46 is located with its first open end 48 at the heating coil 28 of the atomizer. In an assembled state the heating coil 28 or at least part of the heating coil 28 covers part of the capillary tube 46 so that the liquid inside the glass capillary tube 46 is vaporized by the atomizer 26. To achieve this coverage the position of the heating coil 28 inside the battery portion 12, the position of the liquid reservoir 34 inside the mouth piece portion 14 and the length or shape of the glass capillary tube 46 is matched to one another. In FIG. 12, the capillary tube and the heating coil are separate when disassembled, and only when the device is assembled they are brought in contact. Alternatively, the removable mouthpiece portion may also include the heating coil 28, such that it is easier to ensure stable operation, and each time the reservoir is replaced a new heating coil is used.

A guiding portion 68 with a central passage 70 adapted for accommodating the glass capillary tube 46 is provided at an end or end face of the battery portion 12. During use of the electronic cigarette 10 the aerosol created by the heating coil 28 flows around the liquid reservoir 34. In order to allow flow of the aerosol from the atomizer 26 to an air inhalation port 36 of the mouth piece portion 14 the guiding portion 68 includes channels adapted for passing the aerosol through. Alternatively, the guiding portion 68 does not cover the whole cross-section of the battery portion 12 thereby leaving passages for the aerosol open. The mouth piece or mouth piece portion 14 and the e-cigarette 10 may have the advantage that the complete liquid reservoir 34 including the glass capillary tube 46 can easily be removed and replaced. Further, the liquid reservoir 34 may be part of a refillable tank system. The guiding portion 68 may also include a connection element for connecting the battery portion 12 and the mouth piece portion 14. It may also be possible to omit the guiding portion 68. In such case the atomizer 26 may guide the glass capillary tube 46 of the liquid reservoir 34. A first side or surface 58 of the liquid reservoir 34 may define an end stop so that the second open end 52 of the glass capillary tube 46 is located at a defined position with respect to the atomizer 26 or its heating coil 28.

Figure 13:
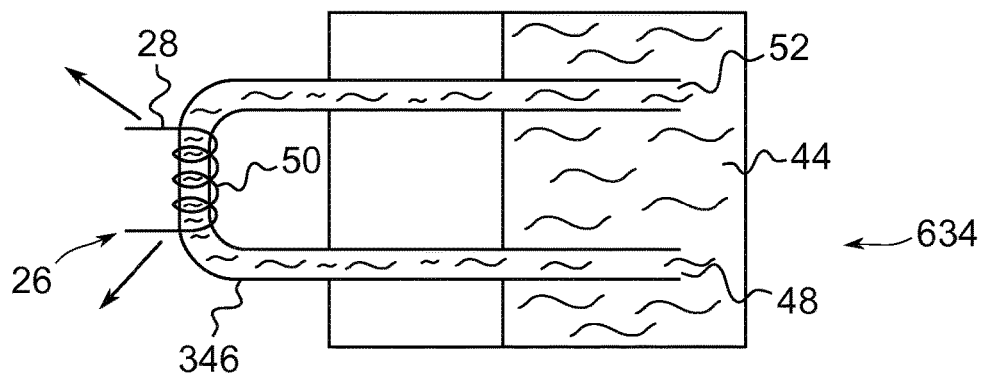
FIG. 13 is a schematic illustration of a further exemplary embodiment of a liquid reservoir.

FIG. 13 shows a further embodiment of the liquid reservoir 634. While in the above embodiments the liquid 44 flows from the first open end 48 of the glass capillary tube towards the second open end 52 of the glass capillary tube, the second open end 52 of the glass capillary tube 346 is also arranged inside the liquid reservoir 634. Accordingly, liquid 44 is drawn from both open ends 48 and 52 towards the outlet portion 50 of the glass capillary tube 346. A heating wire or heating coil 28 of the atomizer is arranged, in this embodiment wound around, the outlet portion 50 of the glass capillary tube 346. This embodiment may have the advantage that the liquid supply to the heating wire 28 is improved. The arrangement of both open ends 48 and 52 inside the liquid reservoir 634 and the resulting two flow paths for the liquid towards the outlet portion 50 provides redundancy. Further, the provision of liquid 44 from both sides towards the outlet portion 50 may result in more even supply of liquid 44.

Figure 14:
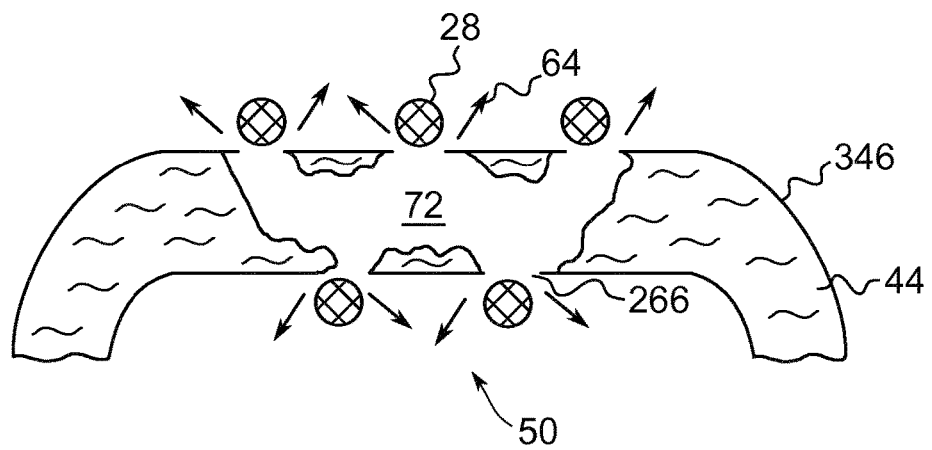
FIG. 14 is a schematic illustration of a part of a further glass capillary tube.

FIG. 14 shows the outlet portion 50 of the glass capillary tube 346 of FIG. 13 in greater detail. The wires 28 of the atomizer are wound around the glass body of the glass capillary tube 346. The outlet portion 50 has the shape of a straight hollow cylinder. Curved portions of the glass capillary tube 346 delimit the outlet portion 50 at both sides. Openings 266 are provided at the outlet portion 50 inside the wall of the glass capillary tube 346. The openings 266 are arranged directly underneath each wire or winding 28. The diameter or size of an opening 266 is large enough to allow aerosol or fluid droplets 64 to leave the capillary tube 346 and small enough to prevent leakage of the liquid 44 from the glass capillary tube 346.

The heat emitted from the heating wire 28 vaporizes the liquid 44 thereby generating fluid droplets 64 which leave the glass capillary tube 346 thereby leaving one or more open spaces 72. Due to capillary force of the glass capillary tube 346 further liquid 44 is drawn into the open space 72 thereby guaranteeing continuous supply of the heating wire 28 with liquid 44.

While the openings 266 are depicted in one single sectional plane the openings may be distributed over the circumference of the glass capillary tube 346. Further, at least one or all of the openings 266 may be arranged not directly underneath a heating wire 28 but beside a heating wire 28. For example, the openings 266 may be arranged between two neighboring heating wires or windings 28.

Figure 15:
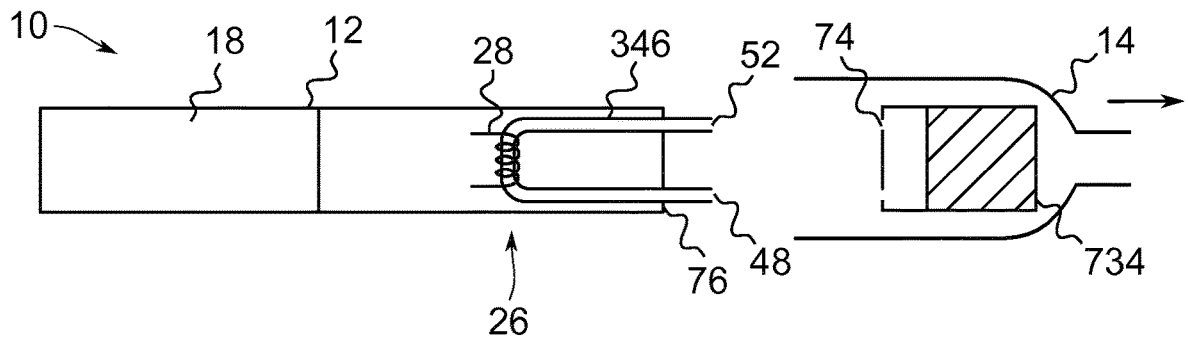
FIG. 15 is a schematic cross-sectional illustration of a further exemplary e-cigarette.

FIG. 15 shows a further exemplary embodiment of an e-cigarette 10. The e-cigarette 10 includes a battery portion 12 with battery 18 and atomizer 26 as well as mouth piece portion 14 including a liquid reservoir 734. According to this embodiment the glass capillary tube 346 is part of the atomizer 26. This implies that the glass capillary tube 346 and the heating coil 28 are permanently connected or engaged. The liquid reservoir 734 and the glass capillary tube 346, however, are detachable. The two open ends 48 and 52 of the glass capillary tube 346 can be inserted into the liquid reservoir 734 through respective ports 74. The glass capillary tube 346 extends through an end face 76 of the battery portion 12.

The two ports 74 may be sealed by a sealing foil or a membrane. At least one of the sealing foil or membrane and the glass capillary tube 346 is adapted for piercing or displacing the sealing foil or membrane. The detachable arrangement may also be implemented for a glass capillary tube having only one end arranged inside the liquid reservoir. In such arrangement only one port 74 may be provided. The end face 76 may provide an end stop allowing exact and reliable positioning of the open ends 48 and 52 of the glass capillary tube 346 inside the liquid reservoir 734. Alternatively, such an end stop may be provided at the glass capillary tube 346 for example in form of a collar.

Figure 16:
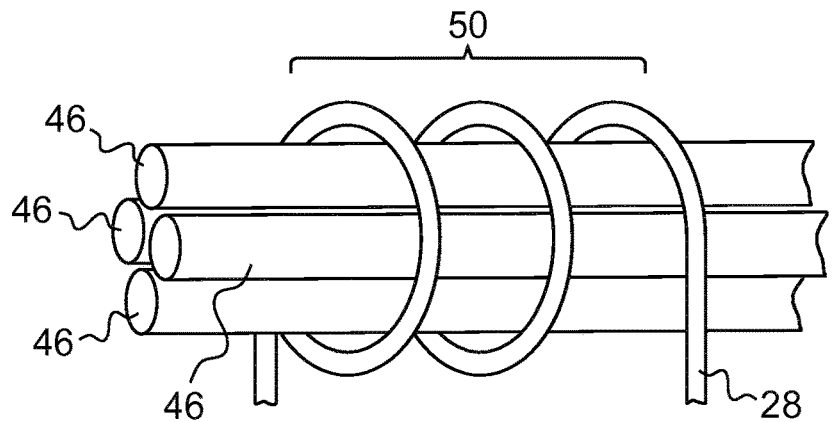
FIG. 16 is a schematic illustration of a part of a further glass capillary tube.

FIG. 16 shows a further embodiment of a plurality of glass capillary tubes 46 and a heating wire 28. The heating wire 28 of the atomizer is wound around the plurality of glass capillary tubes 46 at respective outlet portions 50 of the glass capillary tubes 46. According to this embodiment four glass capillary tubes 46 are provided. The four glass capillary tubes 46 extend in parallel at least at their respective outlet portions 50 which can be defined as a single common outlet portion 50. At least in the area of the outlet portion 50 the four capillary tubes 46 extend in parallel. Such embodiment may have the advantage that liquid supply is improved because of the plurality of glass capillary tubes 46. It may be possible that more than one liquid reservoir is attached to or connected with the plurality of glass capillary tubes 46. Such arrangement may allow mixture of different fluids or liquids at the heating coil 28. Further, a different number of glass capillary tubes 46 may be provided. For example, a number of two, three or six glass capillary tubes 46 may be provided.

Figure 17:
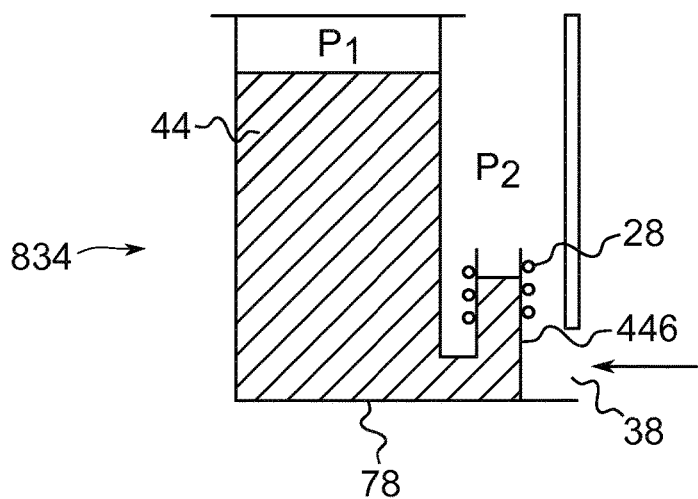
FIG. 17 is a schematic illustration of a further exemplary embodiment of a liquid reservoir.

FIG. 17 shows a further embodiment of a liquid reservoir 834. The liquid reservoir 834 is a pressurized system which means here that the liquid 44 can only escape from the liquid reservoir 834 through the capillary tube 446. Besides the opening of the capillary tube 446 the liquid reservoir 834 is sealed.

The capillary tube 446 is connected with the liquid reservoir 834 or the two elements may be formed integrally. The connection between the capillary tube 446 and the liquid reservoir 834 is airtight so that no air can enter the liquid reservoir 834.

The liquid reservoir 834 has a height measured from a base plate 78 of the liquid reservoir 834 that is larger than the height of the capillary tube 446, preferably by two to three times. The width or radius of the liquid reservoir 834 is also larger, preferably by two to ten times and most preferably by two to six times. Such dimensions allow for good pressure situation and prevent spitting of liquid out of the capillary tube 446.

Spitting is prevented when the height of the liquid 44 inside the capillary tube 446 is kept constant in the range of the heating coil 28 and not above it.

During use the liquid 44 flows out of the liquid reservoir 834 via the capillary tube 446. The liquid 44 flows until the negative pressure p1 is sufficient to stop the flow. The negative pressure is lower than the ambient pressure p2 inside the e-cigarette. Ambient air enters into the e-cigarette via the air inlet 38.

When a puff is taken, an under pressure is created at p2 which causes liquid 44 to rise in the capillary tube. Such action further increases the under pressure p1 inside the liquid reservoir 834. When the puff is taken the heating coil 28 is activated and the excess liquid is vaporized. At the end of the puff, p2 returns to atmospheric pressure which causes an air bubble to enter the capillary tube 446 and further into the liquid reservoir 834. The air bubble reduces the under pressure p1 until it returns to its initial value required to keep the liquid level inside the capillary tube 446 constant. Thus, a pressure balance is achieved After several uses or puffing actions the bubbles rise to fill the upper part of the liquid reservoir 834 and the height of liquid 44 inside the liquid reservoir 834 decreases. The liquid level inside the capillary tube 446 however, is kept constant.

The air inlet 38 reduces the pressure exerted on the surface of the liquid inside the capillary tube 446. Therefore, the amount of liquid drawn into the capillary tube 446 with each puff can be adjusted by changing the ratio between the areas or cross sections of the capillary tube 446 and the air inlet 38. This adjustment may further improve stability of the liquid height inside the capillary tube 446. The adjustment may be achieved by restricting the opening area of the air inlet 38.

While various embodiments of the present invention have been described in conjunction with the figures it is appreciated that embodiments or certain parts of the embodiments may be combined. Especially, the embodiments of the liquid reservoirs, the capillary tubes and/or the heating coils may be combined or substituted in single embodiments.

In summary, in one aspect the mouthpiece adapted for an electronic smoking device has a battery portion including an electric power source and an atomizer/liquid reservoir portion having a mouthpiece opening in an end. The electronic smoking device further includes a liquid reservoir for accommodating a liquid and a glass capillary tube, wherein the glass capillary tube comprises a first open end arranged inside the liquid reservoir and an outlet portion, wherein the glass capillary tube is adapted to transport liquid from the first open end to the outlet portion by capillary force. The electronic smoking device further includes an atomizer arranged at the outlet portion such that is operable to vaporize liquid at the outlet portion to create an aerosol.

Providing liquid without a wick may have the advantage of cleaner incineration or vaporization as not parts of a fabric of the wick are subjected to heat. Instead, the glass material of the capillary tube allows for low friction delivery of the liquid and for residue-free vaporization.

The liquid reservoir may be closed. Such liquid reservoir protects the liquid from external influences like ambient air. The only opening is provided by the capillary tube. Through the capillary tube air may enter into the liquid reservoir for under pressure equalisation. During use, under pressure is built up temporarily inside the liquid reservoir as the amount of liquid inside the liquid reservoir is reduced. Pressure equalisation is achieved by air entering through the capillary tube.

The liquid reservoir comprises at least one air inlet. Such liquid reservoir may improve the liquid delivery as no vacuum or negative pressure is built up which may work against the capillary force. The at least one air inlet may be provided by the capillary tube.

The at least one air inlet may have a diameter allowing air to enter into the liquid reservoir and preventing the liquid to escape from the liquid reservoir. Leakage of the fluid may be prevented by simple means.

At least a part of a casing of the liquid reservoir may comprise a semi-permeable membrane allowing air to enter into the liquid reservoir and preventing the liquid to escape from the liquid reservoir. Such membrane may allow even entry of air into the liquid reservoir.

The outlet portion may comprise at least one opening in a peripheral surface of the glass capillary tube. An advantage may be a more even delivery of aerosol.

The outlet portion may comprise at a plurality of openings arranged circumferentially at a peripheral surface of the glass capillary tube. An advantage may be a more even delivery of aerosol.

A heating wire of the atomizer may be arranged in front of the outlet portion. An advantage may be the simple design and the possibility of retrofitting such design into existing electronic cigarettes.

A heating wire of the atomizer may be wound around a peripheral surface of the glass capillary tube at the outlet portion. An advantage may be a more even vaporization of the liquid.

The glass capillary tube and the liquid reservoir may be detachable. An advantage may be greater flexibility in the handling of electronic cigarettes.

The outlet portion may comprise of a second open end of the glass capillary tube. Alternatively, the outlet portion may consist of the second open end of the glass capillary tube. An advantage may be simple production of the tube and easy handling of the components of the electronic cigarette.

A second open end of the glass capillary tube may be arranged inside the liquid reservoir. An advantage may be a more even delivery of the liquid to the atomizer. A further advantage may be reliable delivery of the liquid even when one open end of the glass capillary tube is not covered by liquid.

The electronic smoking device may comprise a plurality of glass capillary tubes, wherein a heating wire of the atomizer is wound around the plurality of glass capillary tubes at the respective outlet portions. An advantage may be an increased number of parallel supply paths or the possibility of connecting different liquid reservoirs to one atomizer. A number of four glass capillary tubes may have the advantage of a good trade off between a maximum of parallel supply paths and easy construction and handling of the electronic cigarette.

The glass capillary tube may be inflexible or rigid. The thickness of the glass wall of the glass capillary tube may be such that no bending of the glass capillary tube is possible. Such embodiment may have the advantage that mechanical stability is enhanced and steady, reliable liquid transportation is provided.

In one aspect the cartomizer operable to be connected to a power supply for an electronic smoking device has an elongated, hollow body having a mouthpiece opening in a first end and a coupling adapted to couple to a battery portion of an electronic smoking device in an opposite second end and a liquid reservoir for accommodating a liquid. The cartomizer further includes a glass capillary tube, wherein the glass capillary tube comprises a first open end arranged inside the liquid reservoir and an outlet portion, wherein the glass capillary tube is adapted to transport liquid from the first open end to the outlet portion by capillary force. Further, the outlet portion is arranged at the second end of the cartomizer such that an atomizer arranged in the battery portion is operable to vaporize liquid at the outlet portion to create an aerosol.

Providing liquid without a wick may have the advantage of cleaner incineration or vaporization as not parts of a fabric of the wick are subjected to heat. Instead, the glass material of the capillary tube allows for low friction delivery of the liquid and for residue-free vaporization.

While this invention has been described in connection with what is presently considered to be practical exemplary embodiments, it is to be understood that the invention is not limited to the disclosed embodiments, but, on the contrary, is intended to cover various modifications and equivalent arrangements included within the scope of the appended claims.

LIST OF REFERENCE SIGNS 10 e-cigarette
12 battery portion
14 atomizer/liquid reservoir portion
16 end cap
18 battery
20 light emitting diode (LED)
22 control electronics
24 airflow sensor
26 atomizer
28 heating coil
30 wick
32 central passage
34, 134, 234, 334, 434, 534, 634, 734, 834 liquid reservoir
36 air inhalation port
38 air inlets
40 air flow path
44 liquid
46, 146, 246, 346, 446 capillary tube
48 first open end
50 outlet portion
52 second open end
54 membrane
56 air inlet
58 first side
60 second side
32 wall
64 fluid droplets
66, 166, 266 opening
68 guiding portion
70 passage
72 open space
74 port
76 end face
78 base plate

The invention claimed is:
1. An electronic smoking device, comprising:
a battery portion including an electric power source;
an atomizer/liquid reservoir portion having a mouthpiece opening in an end;
a liquid reservoir for accommodating a liquid;

a glass capillary tube;

wherein the glass capillary tube comprises a first open end arranged inside the liquid reservoir and an outlet portion, wherein the glass capillary tube is adapted to transport liquid from the first open end to the outlet portion by capillary force, and wherein the outlet portion comprises at least one opening in a peripheral surface of the glass capillary tube; and an atomizer arranged at the outlet portion such that is operable to vaporize liquid at the outlet portion to create an aerosol.

2. The electronic smoking device of claim 1, wherein the liquid reservoir is closed.

3. The electronic smoking device of claim 1, wherein the liquid reservoir comprises at least one air inlet.

4. The electronic smoking device of claim 3, wherein the at least one air inlet has a diameter allowing air to enter into the liquid reservoir and preventing the liquid to escape from the liquid reservoir.

5. The electronic smoking device of claim 1, wherein at least a part of a casing of the liquid reservoir comprises a semi-permeable membrane allowing air to enter into the liquid reservoir and preventing the liquid to escape from the liquid reservoir.

6. The electronic smoking device of claim 1, wherein the outlet portion comprises at a plurality of openings arranged circumferentially at a peripheral surface of the glass capillary tube.

7. The electronic smoking device of a claim 1, wherein a heating wire of the atomizer is arranged in front of the outlet portion.

8. The electronic smoking device of claim 1, wherein a heating wire of the atomizer is wound around a peripheral surface of the glass capillary tube at the outlet portion.

9. The electronic smoking device of claim 1, wherein the glass capillary tube is detachable from the liquid reservoir.

10. The electronic smoking device of claim 1, wherein the outlet portion comprises a second open end of the glass capillary tube.

11. The electronic smoking device of claim 1, wherein a second open end of the glass capillary tube is arranged inside the liquid reservoir.

12. The electronic smoking device of claim 1, comprising a plurality of glass capillary tubes having respective outlet portions, wherein a heating wire of the atomizer is wound around the plurality of glass capillary tubes at the respective outlet portions.

13. The electronic smoking device of claim 1, wherein the glass capillary tube is inflexible.

14. A cartomizer operable to be connected to a power supply for an electronic smoking device comprising:

an elongated, hollow body having a mouthpiece opening in a first end and a coupling adapted to couple to a battery portion of an electronic smoking device in an opposite second end;

a liquid reservoir for accommodating a liquid;

a glass capillary tube;

wherein the glass capillary tube comprises a first open end arranged inside the liquid reservoir and an outlet portion, wherein the glass capillary tube is adapted to transport liquid from the first open end to the outlet portion by capillary force, and wherein the outlet portion comprises at least one opening in a peripheral surface of the glass capillary tube; and wherein the outlet portion is arranged at the second end of the cartomizer such that an atomizer arranged in the battery portion is operable to vaporize liquid at the outlet portion to create an aerosol.

* * * * *